(12) United States Patent
Nuccio-Youngs

(10) Patent No.: US 8,257,090 B1
(45) Date of Patent: Sep. 4, 2012

(54) RESIDUAL LIMB MODEL

(76) Inventor: Theresa Nuccio-Youngs, Gaithersburg, MD (US)

( * ) Notice: Subject to any disclaimer, the term of this patent is extended or adjusted under 35 U.S.C. 154(b) by 0 days.

(21) Appl. No.: 12/903,985

(22) Filed: Oct. 13, 2010

Related U.S. Application Data

(62) Division of application No. 11/880,767, filed on Jul. 24, 2007, now Pat. No. 7,837,474.

(51) Int. Cl.
*A61F 2/74* (2006.01)
*A61F 2/60* (2006.01)
*A61F 2/80* (2006.01)
*G09B 23/28* (2006.01)

(52) U.S. Cl. .............. 434/267; 623/27; 623/28; 623/33; 623/36; 623/37

(58) Field of Classification Search .................. 434/267; 623/27–38
See application file for complete search history.

(56) References Cited

U.S. PATENT DOCUMENTS

| | | | |
|---|---|---|---|
| 2,202,598 A | 5/1940 | Peterson | |
| 4,704,129 A | 11/1987 | Massey | |
| 5,163,965 A | 11/1992 | Rasmusson et al. | |
| 5,246,464 A | 9/1993 | Sabolich | |
| 5,258,037 A | 11/1993 | Caspers | |
| 5,314,497 A | 5/1994 | Fay et al. | |
| 5,507,834 A * | 4/1996 | Laghi | 623/36 |
| 5,549,709 A | 8/1996 | Caspers | |
| 5,658,353 A | 8/1997 | Layton | |
| 5,735,906 A | 4/1998 | Caspers | |
| 5,768,134 A | 6/1998 | Swaelens et al. | |
| 5,904,722 A | 5/1999 | Caspers | |
| 6,585,744 B1 | 7/2003 | Dean et al. | |
| 6,936,073 B2 | 8/2005 | Karason | |
| 2003/0078674 A1 | 4/2003 | Phillips | |
| 2003/0181990 A1 | 9/2003 | Phillips | |
| 2004/0098136 A1 | 5/2004 | Caspers | |
| 2007/0055383 A1 | 3/2007 | King | |
| 2009/0011394 A1 | 1/2009 | Meglan et al. | |

* cited by examiner

*Primary Examiner* — Thomas J Sweet
*Assistant Examiner* — Jacqueline Woznicki
(74) *Attorney, Agent, or Firm* — Doster Greene, LLC

(57) ABSTRACT

A residual limb model may be a model of a residual limb. A residual limb model may include a residual limb portion and a bladder complementary in shape to the residual limb portion. A prosthesis donning and doffing training system may include a check socket and a residual limb model complementary in shape to the check socket. A method of training in the care of a residual limb may include providing a residual limb model and training in the care of a residual limb using the residual limb model. A method of training in the donning and doffing of a prosthesis may include providing a prosthesis training system and training in the donning and doffing of a prosthesis using the prosthesis training system.

3 Claims, 9 Drawing Sheets

RESIDUAL LIMB MODEL

This application is a divisional of application of Ser. No. 11/880,767, filed Jul. 24, 2007, currently pending. The entire contents of the above-identified application is hereby incorporated by reference.

BACKGROUND

1. Field

Embodiments of the present invention relate generally to training models and, more particularly, to residual limb models.

2. Description of the Related Art

Amputation of one or more limbs is a reality for many individuals. Amputation typically involves the removal of a limb by trauma or surgery. The portion of the limb remaining after amputation may be referred to as a residual limb.

A residual limb requires special care, especially immediately following amputation. For example, a residual limb will develop edema and require treatment for shrinkage, such as proper wrapping with an elasticized bandage strip, such as an AC brand elasticized bandage or use of a stump shrinker. Incisional massage is another example of required special care.

Conventionally, training and practice in the shrinkage care of a residual limb may include having an amputee or caregiver practice on or with an actual residual limb. This may injure the residual limb or delay healing of an incision, if performed improperly. Further injury or delayed healing can create additional medical issues for an amputee, including, for example, re-amputation.

An amputee may use a prosthetic device. An amputee may use a sock or socks in conjunction with a prosthetic device. Generally, an amputee will wear a sock or socks over their residual limb. The number of socks (or the thickness of the socks which may be referred to as sock ply) is affected by the amputee's edema. Donning and doffing of a prosthetic device, and mastering the concept of sock ply can also be difficult tasks to learn. Further, due to the non-transparent nature of prosthetic devices, it may not be possible for an amputee to visually see proper insertion of a residual limb into a check socket.

As can be seen, there is a need for improved training and practice in the care of residual limbs. There is also a need for improved training in donning and doffing of prosthetic devices.

BRIEF SUMMARY

According to an aspect of the invention, a residual limb model is provided. The residual limb model may include a residual limb portion and a bladder complementary in shape to the residual limb portion.

According to another aspect of the invention, a residual limb model is provided. The residual limb model may include a plastic residual limb portion, a soft cover over at least a portion of the plastic residual limb portion, and a bladder between the plastic residual limb portion and the soft cover to simulate edema in a residual limb.

According to another aspect of the invention, a residual limb model is provided. The residual limb model may include a residual limb portion, the residual limb portion being formed of at least one member of the group consisting of urethane and silicone, and a bladder inside of the residual limb portion to simulate edema in a residual limb.

According to another aspect of the invention, a prosthesis donning and doffing training system is provided. The prosthesis donning and doffing training system may include a check socket and a residual limb model complementary in shape to the check socket.

According to another aspect of the invention, a method of training in the care of a residual limb is provided. The method may include providing a residual limb model and training in the care of a residual limb using the residual limb model.

According to another aspect of the invention, a method of training in the donning and doffing of a prosthesis is provided. The method may include providing a prosthesis training system and training in the donning and doffing of a prosthesis using the prosthesis training system. The prosthesis training system may include a check socket and a residual limb model.

The foregoing and other aspects will become apparent from the following detailed description when considered in conjunction with the accompanying drawing figures.

DETAILED DESCRIPTION

Figure 1:
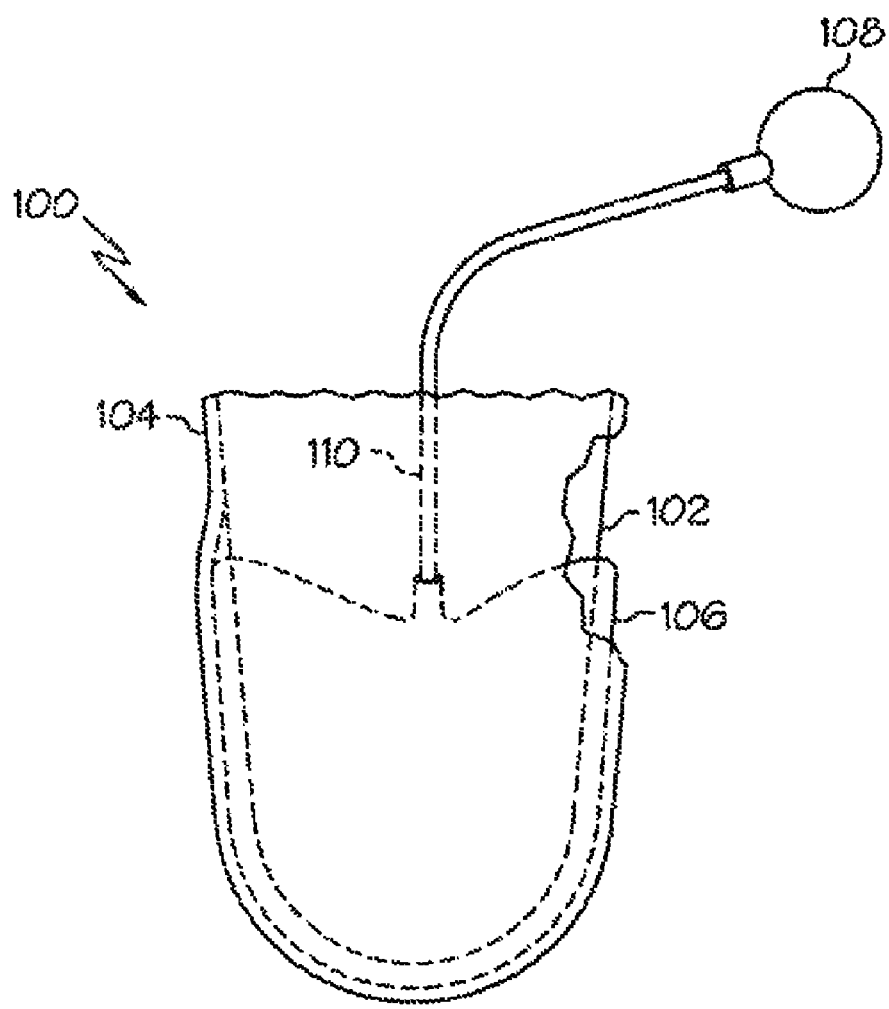
FIG. 1 is a perspective view of a residual limb model according to an embodiment of the present invention.

Reference will now be made in detail to embodiments of the present invention, examples of which are illustrated in the accompanying drawings, wherein like reference numerals refer to the like elements throughout. The embodiments are described below to explain the present invention by referring to the figures.

FIG. 1 is a perspective view of a residual limb model 100 according to an embodiment of the present invention. The residual limb model 100 may be a model of a residual limb (the part of a limb that remains following amputation of that limb). The residual limb model 100 generally may include a residual limb portion 102, a soft cover 104, a bladder 106 between the residual limb portion 102 and the soft cover 104, and a pump 108. In an alternative embodiment shown in FIG. 13, a bladder 1306 may be located inside of a residual limb portion 1302. In such an alternative embodiment, a soft cover may not be included. Returning to FIG. 1 and in FIG. 12, the residual limb model 100, 1200 may, as discussed below, be used with an optional check socket.

Figure 12:
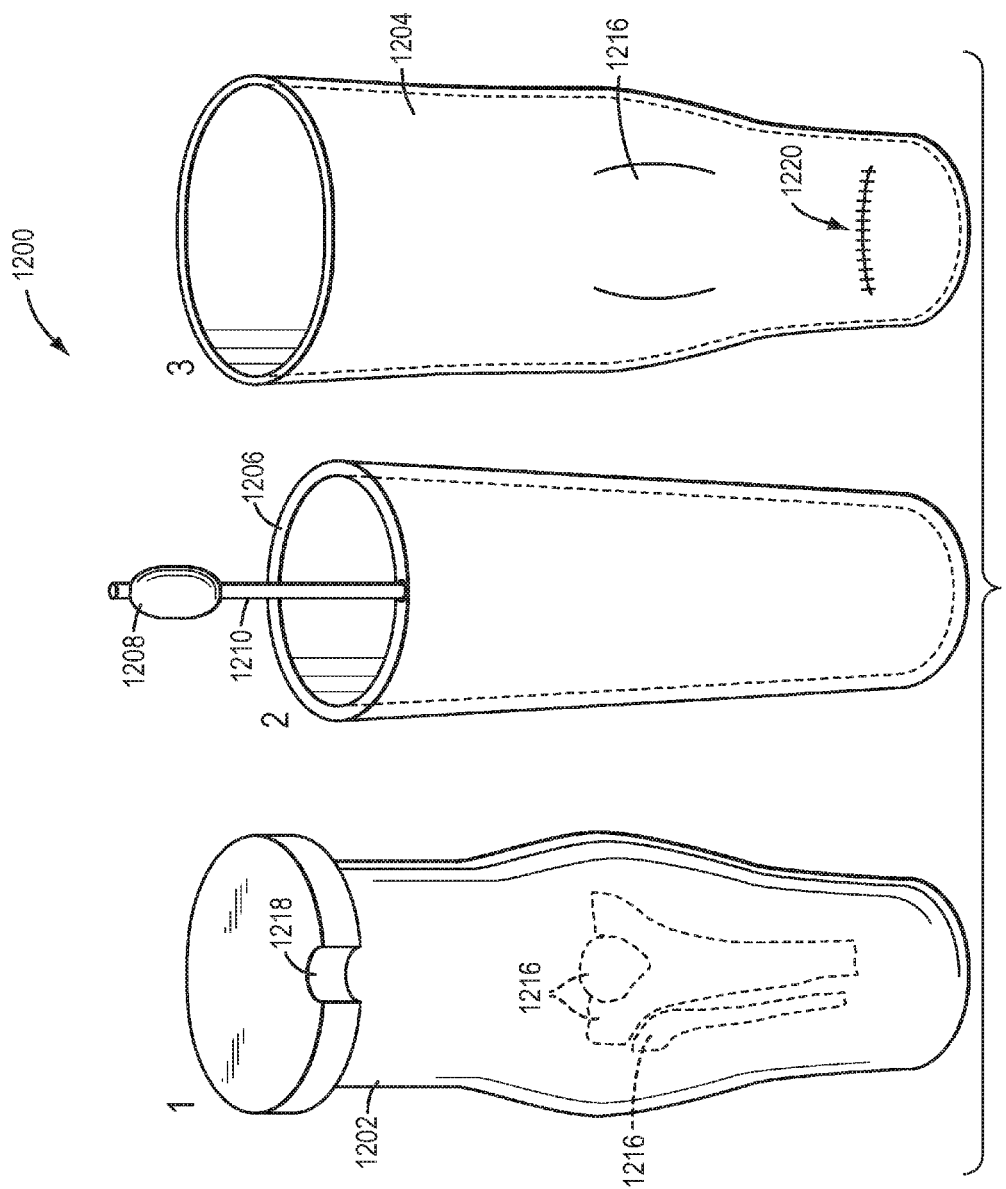
FIG. 12 is an exploded view of a residual limb model according to an embodiment of the present invention.
Figure 13:
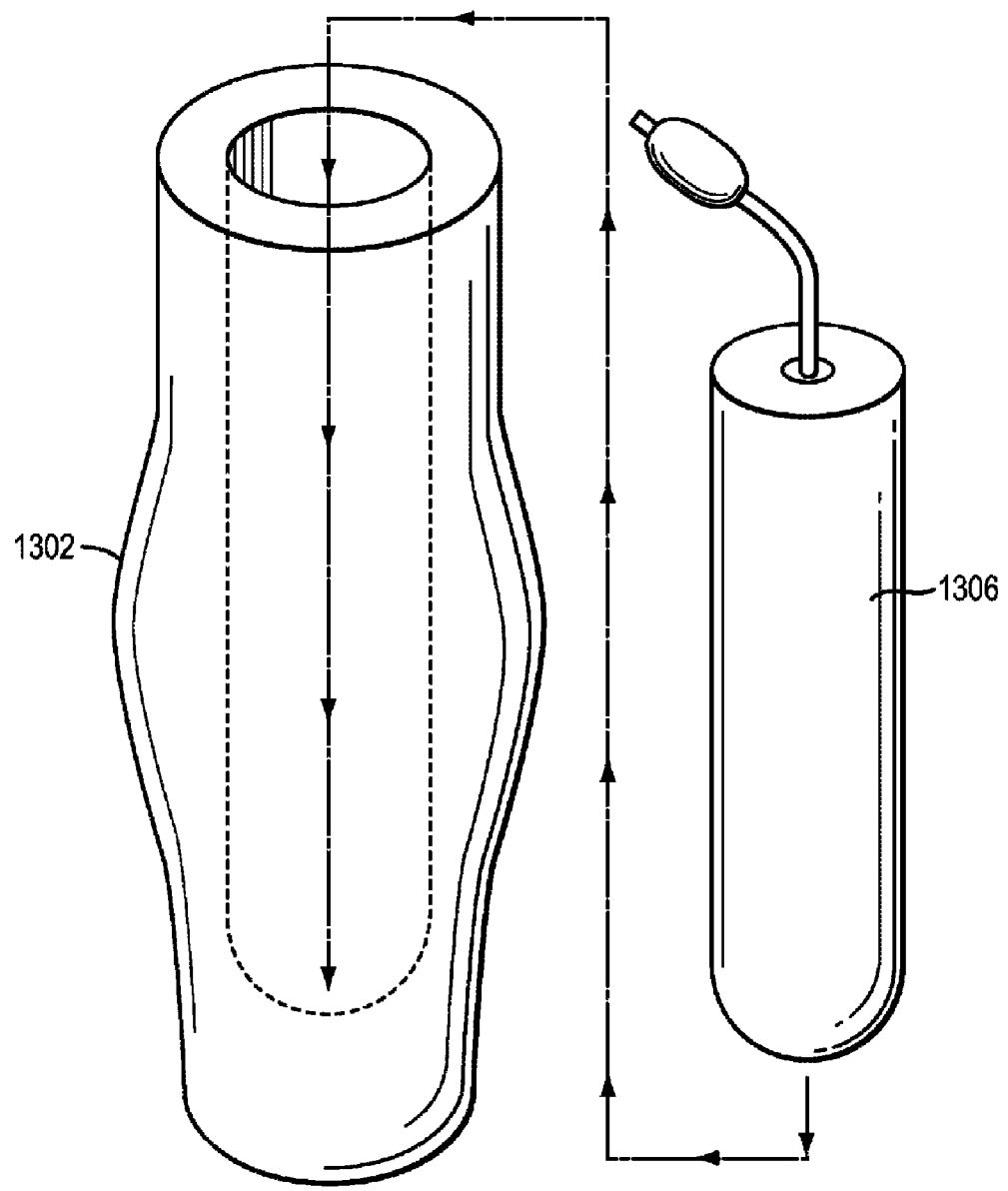
FIG. 13 is an exploded view of a residual limb model according to another embodiment of the present invention.

In FIGS. 1 and 12, the residual limb portion 102, 1202 may be shaped like a residual limb. The residual limb portion 102, 1202 may be solid. The residual limb portion 102, 1202 may be formed of plastic including polypropylene, however, other materials such as other plastics may be used. In an alternative embodiment, the residual limb portion 102, 1202 may be formed of an expandable and flexible material such as urethane or silicone. The residual limb portion 102 may appear life-like, and may include simulated bony prominences. The residual limb portion 102, 1202 may include a cavity 1218 to house a tube 110, 1210 running between the bladder 106, 1206 and the pump 108, 1208. In an alternative embodiment, a tube may extend outwardly from a bladder to a pump.

The soft cover 104, 1204 may cover the residual limb portion 102, 1202 and the bladder 106, 1206. The soft cover 104, 1204 may be formed of latex or silicone. The soft cover 104, 1204 may be skin-like. The soft cover 104, 1204 may be tightly wrapped around the residual limb portion 102, 1202 and the bladder 106, 1206 to form a unitary model.

The bladder 106 may be formed of expandable materials such as plastic, nylon and rubber. The bladder 106 may be wrapped around the bottom and sides of the residual limb portion 102. The bladder 106 may be attached to the pump 108 by a tube 110. The pump 108 may inflate or deflate the bladder 106 to simulate, for example, volume changes in a residual limb. In an embodiment, the pump 108 may be a bulb-shaped pump. The bladder 106 and the pump 108 may allow for simulation of edema or shrinkage that occurs in a residual limb. The pump 108 and the tube 110 may be movable relative to the residual limb portion 102.

Figure 3:
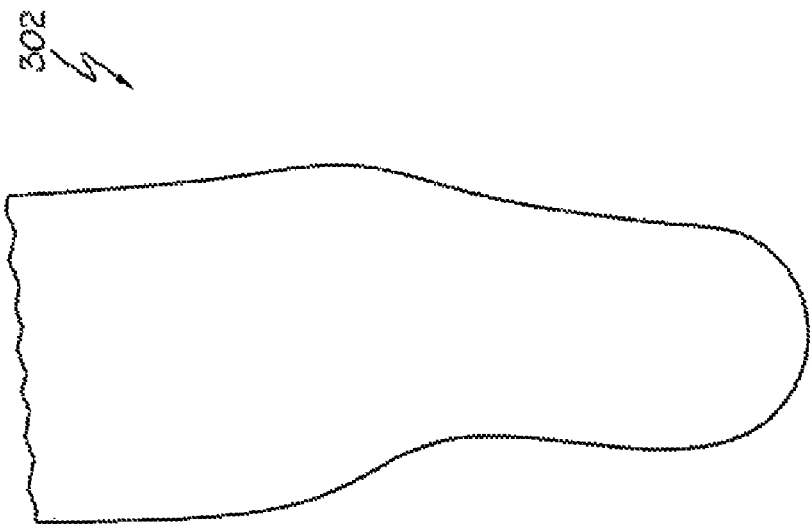
FIG. 3 is a perspective view of a transtibial (TT) residual limb portion of a residual limb model according to another embodiment of the present invention.
Figure 2:
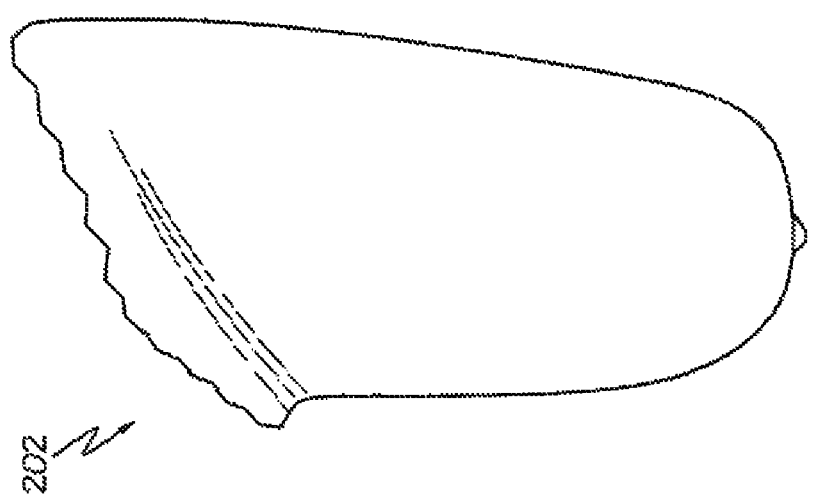
FIG. 2 is a perspective view of a transfemoral (TF) residual limb portion of a residual limb model according to another embodiment of the present invention.

Various residual limb types may be modeled. For example, a residual limb model may be modeled after a transfemoral (TF) residual limb, occurring after a leg amputation above the knee, or a transtibial (TT) residual limb, occurring after a leg amputation below the knee. FIG. 2 is a perspective view of a TF residual limb portion 202 of a residual limb model according to another embodiment of the present invention. FIG. 3 is a perspective view of a TT residual limb portion 302 of a residual limb model according to another embodiment of the present invention.

Figure 4:
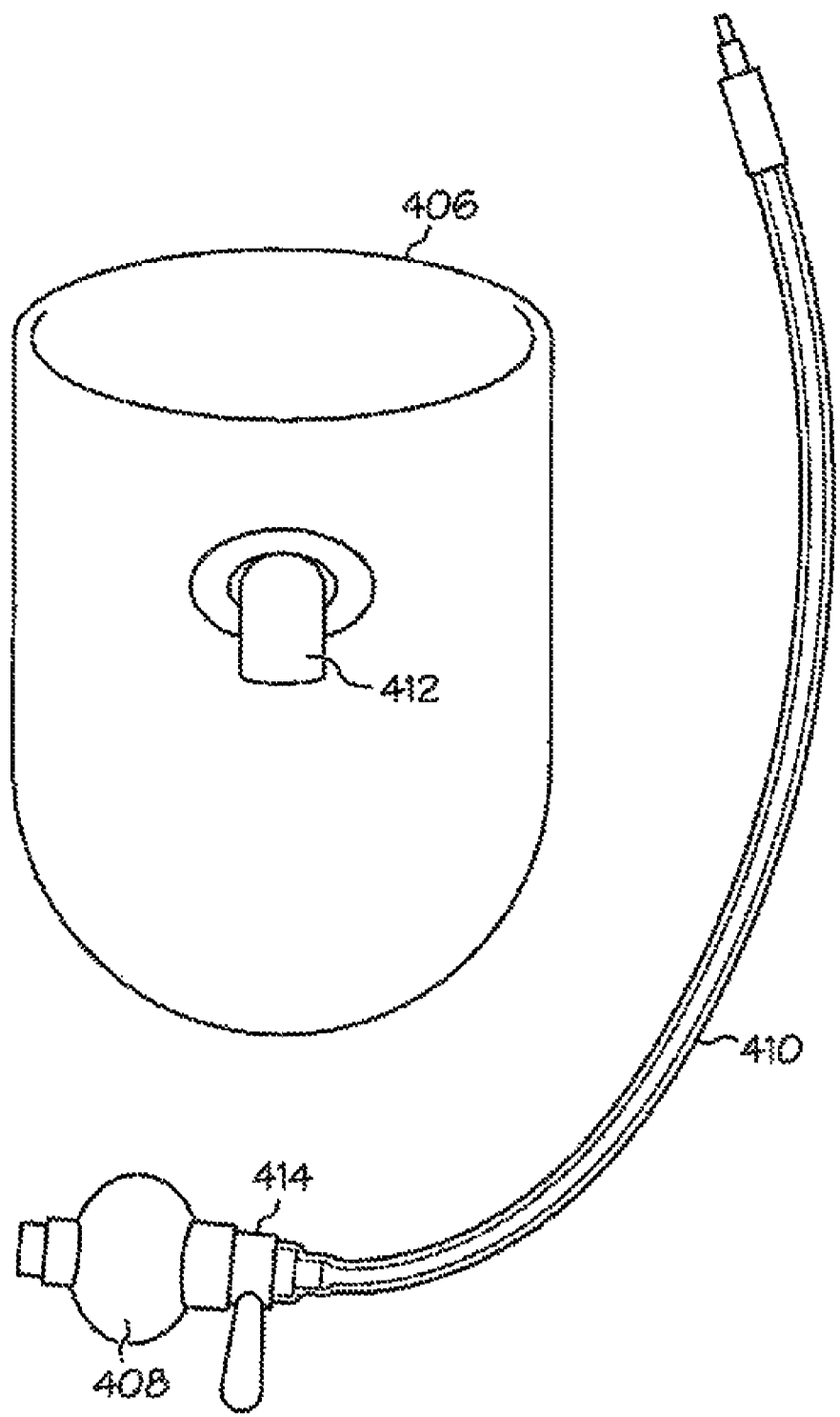
FIG. 4 is a perspective view of a bladder and a pump according to another embodiment of the present invention.

FIG. 4 is a perspective view of a bladder 406 and a pump 408 according to another embodiment of the present invention. The bladder 406 may be formed of plastic. The bladder 406 may be formed in a U or cylindrical shape. The bladder 406 may attached to the pump 408 by a tube 410. The bladder 406 may include a bladder/tube attachment 412 to attach the bladder 406 to the tube 410. The pump 408 may include a pump/tube attachment to attach the pump 408 to the tube 410. The pump 408 and the bladder 406 may form a pneumatic pump system.

Figure 5:
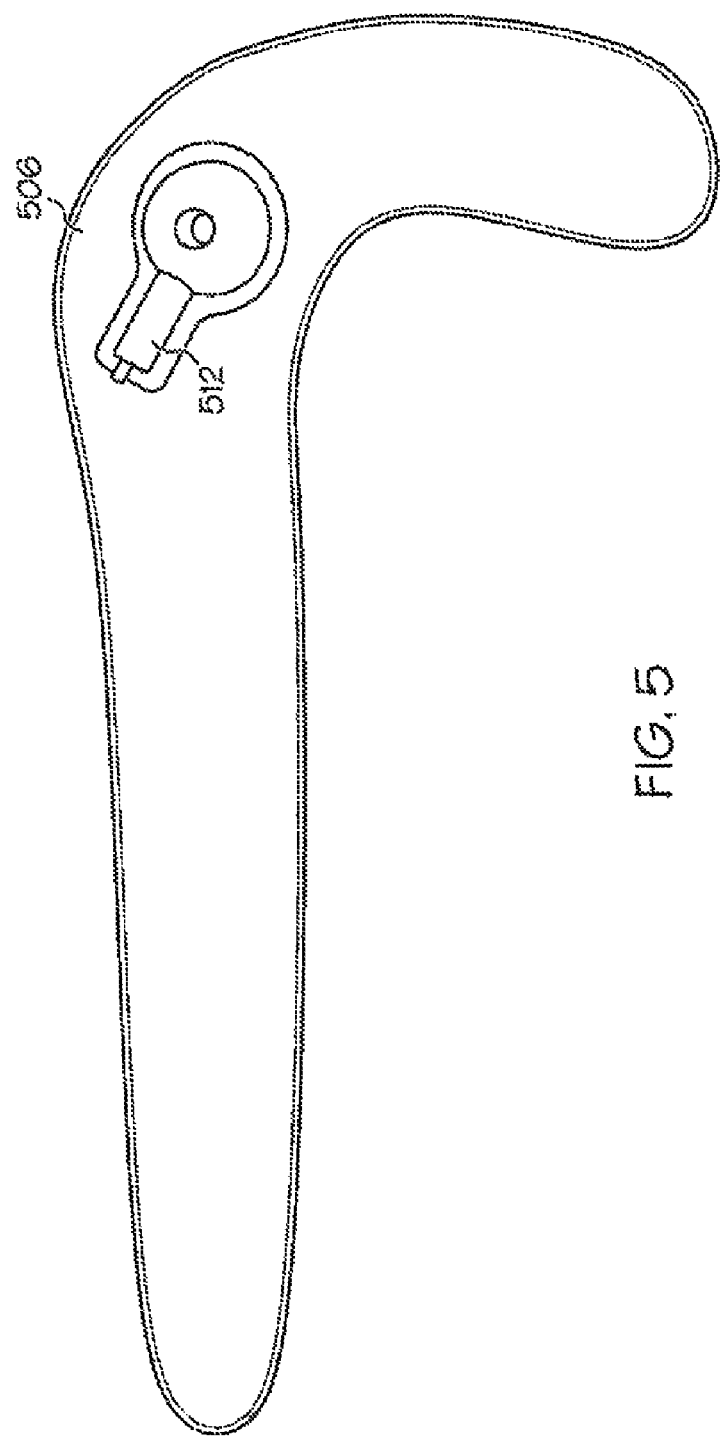
FIG. 5 is a perspective view of a bladder according to another embodiment of the present invention.

FIG. 5 is a perspective view of a bladder 506 according to another embodiment of the present invention. The bladder 506 may be formed generally in an L shape. The bladder 506 may include a bladder/tube attachment 512 to attach the bladder 506 to a tube.

Figure 6:
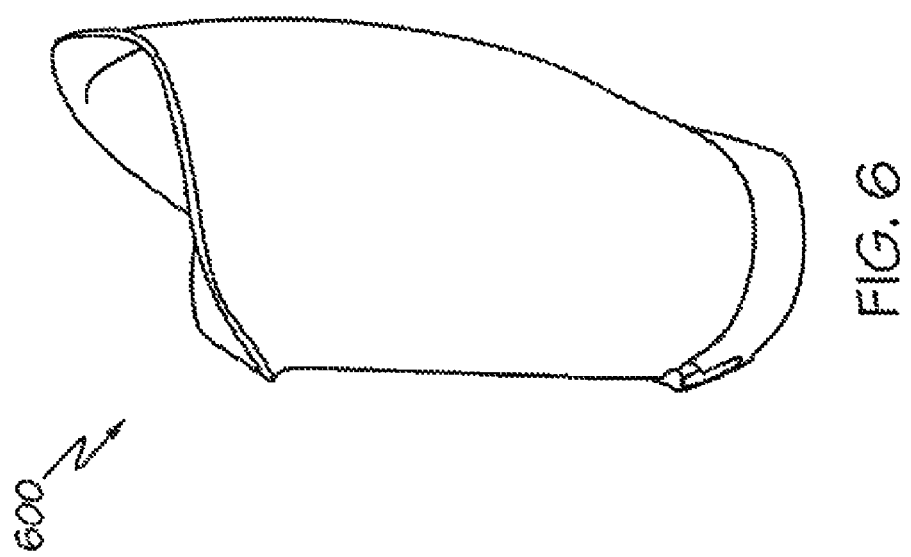
FIG. 6 is a perspective view of TF check socket to receive a residual limb model according to an embodiment of the present invention.

FIG. 6 is a perspective view of TF check socket 600 to receive a residual limb model according to an embodiment of the present invention. The TF check socket 600 may be shaped like a socket part found at the attachment site of a prosthetic device. The TF check socket 600 may be solid. The TF check socket 600 may be formed of plastic, such as a rigid plastic.

Figure 7:
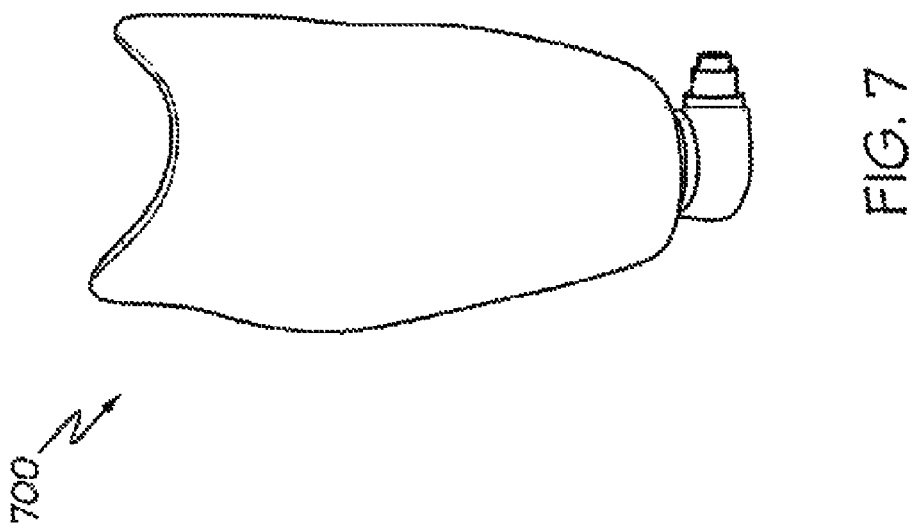
FIG. 7 is a perspective view of a TT check socket to receive a residual limb model according to an embodiment of the present invention.

Exemplary rigid plastics include co-polyesters, such as Durr-Plex, ThermoLy® brand PETG, and Vival® brand PETG. The TF check socket 600 may be clear such that insertion of the residual limb model into the TF check socket 600 may be easily visible through the side of the TF check socket 600. FIG. 7 is a perspective view of a TT check socket 700 to receive a residual limb model according to an embodiment of the present invention.

Figure 8:
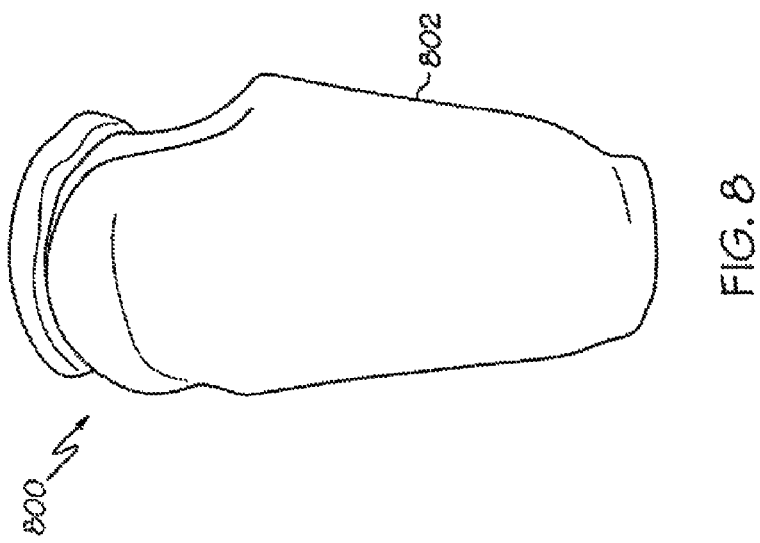
FIG. 8 is a perspective view of a residual limb model with a residual limb sock according to an embodiment of the present invention.

FIG. 8 is a perspective view of a residual limb model 800 with a residual limb sock 802 according to an embodiment of the present invention. The residual limb sock 802 may be placed over the residual limb model 800. The residual limb sock 802 may be formed of wool, however, other materials may be used. The residual limb sock 802 may include an indication of thickness (e.g., 3 ply). An amputee may calculate a total sock ply of multiple socks using such indications.

Figure 9:
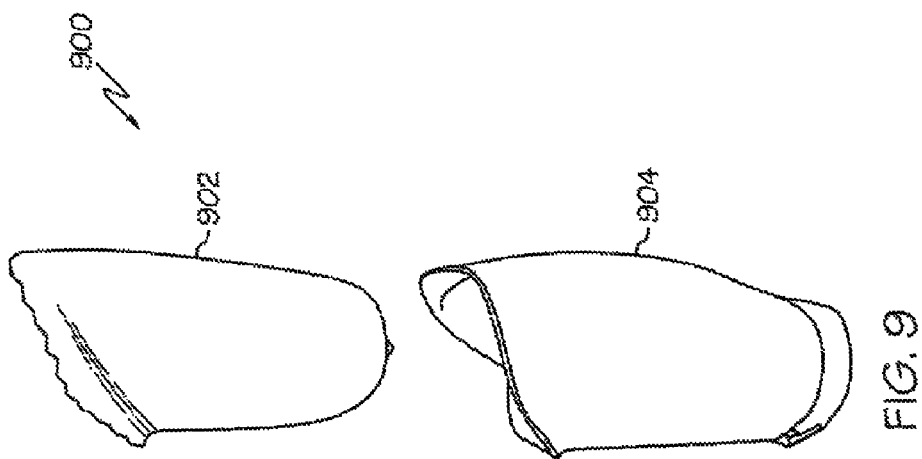
FIG. 9 is a perspective view of a prosthesis training system according to an embodiment of the present invention.

FIG. 9 is a perspective view of a prosthesis training system 900 according to an embodiment of the present invention. The prosthesis training system 900 may include a residual limb portion 902 and a check socket 904. The residual limb portion 902 may include a handle (not shown). The handle may extend outwardly from the top of the residual limb portion 902. The prosthesis training system may be used to train amputees in donning and doffing of a prosthetic device, and to allow amputees to practice donning and doffing of a prosthetic device. A method of training in the donning and doffing of a prosthesis using a residual limb model is discussed below.

Figure 10:
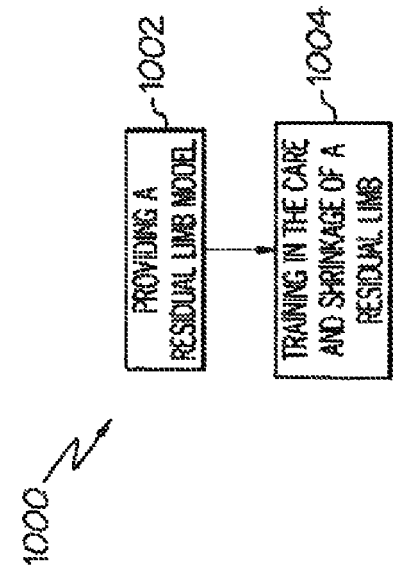
FIG. 10 is a schematic representation of a method of training in the care of a residual limb using a residual limb model, such as the residual limb model of FIG. 1.

FIG. 10 is a schematic representation of a method 1000 of training in the care of a residual limb using a residual limb model, such as the residual limb model 100 of FIG. 1. The process 1000 may include providing 1002 a residual limb model 100, 1200 and training 1004 in the care and shrinkage of a residual limb using the residual limb model 100, 1200. The residual limb model 100, 1200 may include visual indicators to be used in training in the care of a residual limb. For example, a simulated incision marking 1220 may be included. Further, simulated bony prominences 1216 may be included. The residual limb model 100, 1200 may be used to train in the proper application of an elasticized bandage strip, a stump shrinker, a tubular compression bandage or a tubular compression stockinette. The residual limb model 100, 1200 may be used to train in the proper care of an edematous limb, the proper massage of a residual limb, the care of a residual limb incision, or the care of a residual limb scar.

Figure 11:
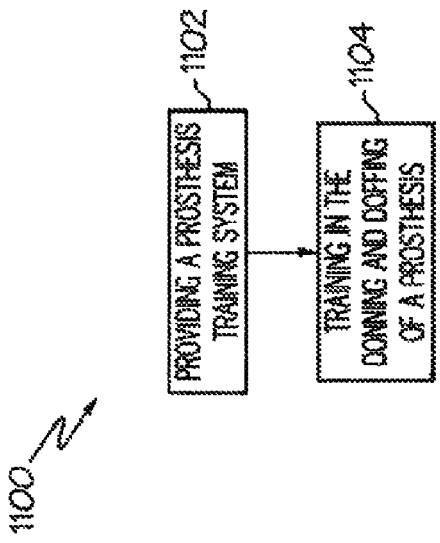
FIG. 11 is a schematic representation of a method of training in the donning and doffing of a prosthesis using a prosthesis training system including a residual limb model, such as the prosthesis training system of FIG. 9.

FIG. 11 is a schematic representation of a method 1100 of training in the donning and doffing of a prosthesis using a prosthesis training system including a residual limb model, such as the prosthesis training system 900 of FIG. 9. The method 1100 may include providing 1102 a prosthesis training system 900 and training 1104 in the donning and doffing of a prosthesis using the prosthesis training system 900. The prosthesis training system 900 may include a check socket and a residual limb model. The prosthesis training system 900 may further include a residual limb sock or socks. The training 1104 in the donning and doffing of a prosthesis may include training in properly applying/removing a sock or socks (thereby adding/removing sock ply.) The check socket may be clear. The prosthesis training system 900, due to the check socket being clear, may be a helpful visual indicator to aid in the proper donning and doffing of the residual limb model into the check socket. The clear check socket may enable the user to determine if there are any wrinkles in the residual limb socks and enable the user to properly line up the limb model to the check socket.

Some of the embodiments have been described with reference to a residual limb model of a human residual leg. However, the invention should not be limited thereto. For example, a residual limb model of a residual arm should be considered to be within the scope of the invention.

Although embodiments of the present invention have been shown and described, it would be appreciated by those skilled in the art that changes may be made in these embodiments without departing from the principles and spirit of the invention, the scope of which is defined in the claims and their equivalents.

What is claimed:

1. A prosthesis device comprising:
a residual limb model comprising a residual limb portion having elastically deformable properties, a substantially hollow internal core forming a cavity, and configured to resemble a residual limb; and
a bladder having a closed, elongated cylindrical body that is complementary in shape to the residual limb portion;
wherein the bladder is removably insertable within the cavity of the residual limb portion such that the bladder substantially fills the cavity of the residual limb model to form a structure configured to be inserted into a check socket to facilitate training in donning and doffing of a prosthesis and training in care of the residual limb, and the bladder being configured such that inserting the elongated cylindrical body into the cavity substantially fills an entire volume of the cavity to form a substantially filled cavity such that inflation of the bladder outwardly expands an elastic outer layer of the residual limb portion, and deflation of the bladder inwardly contracts the elastic outer layer of the residual limb portion to simulate at least one of a volume change in the residual limb, edema in the residual limb, and shrinkage in the residual limb;
wherein the simulated volume change in the residual limb portion trains an amputee to manage and control limb volume changes within the residual limb;
wherein the simulated edema in the residual limb portion trains the amputee to care for an edematous limb; and
wherein the simulated shrinkage in the residual limb portion trains the amputee to shrink the residual limb and perform skin care in preparation for the prosthesis; and
wherein the check socket is configured to retain at least a portion of the structure of the residual limb model such that the residual limb model is complementary in shape to the check socket.

2. The prosthesis device of claim 1, wherein the check socket is clear.

3. The prosthesis device of claim 1, further comprising:
a residual limb sock,
wherein the residual limb sock is complementary in shape to the model of the residual limb portion.

\* \* \* \* \*